United States Patent [19]

Milner

[11] Patent Number: 4,517,129
[45] Date of Patent: May 14, 1985

[54] PROCESS FOR THE PREPARATION OF CYANOTETRACHLOROBENZENES

[75] Inventor: David J. Milner, Manchester, England

[73] Assignee: Imperial Chemical Industries PLC, London, England

[21] Appl. No.: 575,997

[22] Filed: Feb. 1, 1984

[30] Foreign Application Priority Data

Feb. 15, 1983 [GB] United Kingdom ............... 8304161

[51] Int. Cl.$^3$ .......................................... C07C 121/50
[52] U.S. Cl. ................................................. 260/465 G
[58] Field of Search .................................... 260/465 G

[56] References Cited

PUBLICATIONS

Chemical Abstracts, 89, 42721 (1978).
Letsinger and Hautala, Tet. Lett., 4205 (1969).
Lok et al., Tet. Lett., 4701 (1970).
Hashem, Rev. Roumaine Chim., 27, 429 (1982).
Bunnett and Zahler, Chim. Rev. 49 273 (1951).
JACS, 88 2884 (1966).
JACS, 43, 898 (1921).
Finger and Kruse, JACS 78, 6034 (1978).

*Primary Examiner*—Dolph H. Torrence
*Attorney, Agent, or Firm*—Cushman, Darby & Cushman

[57] ABSTRACT

Cyanotetrachlorobenzenes, especially ortho- and para-dicyanotetrachlorobenzenes, are prepared by reacting in a liquid medium at 20°–100° C. a corresponding nitrotetrachlorobenzene with, in solution, an inorganic cyanide. Preferably the liquid medium is a two-phase water/water-immiscible organic solvent system, e.g. water/chloroform, a phase transfer catalyst is present and the inorganic cyanide is an alkali metal or alkaline earth metal cyanide.

The compounds are useful chemical intermediates in the synthesis of, for instance, pesticidal compounds.

7 Claims, No Drawings

PROCESS FOR THE PREPARATION OF CYANOTETRACHLOROBENZENES

The invention relates to a process for the preparation of cyanotetrachlorobenzenes.

According to the present invention there is provided a process for the preparation of a compound of formula (I):

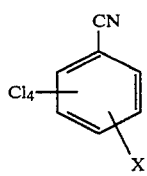

in which X is CN or, when X is in a position meta to the CN group in formula (I), CN or $NO_2$, which process comprises reacting in a liquid medium a compound of formula (II):

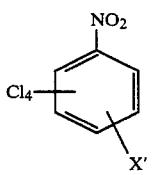

in which X', which is in a corresponding position to X, is CN or $NO_2$, with, in solution, an inorganic cyanide, whereby at least one $NO_2$ group is replaced by a cyano group. Preferably X and X' are in positions ortho or, especially, para to the CN group of formula (I) and $NO_2$ group of formula (II), respectively.

The invention is of particular value for the preparation of dicyanotetrachlorobenzenes in which the two cyano groups are attached to the benzene ring in positions ortho or para to each other from the corresponding dinitrotetrachlorobenzenes.

The inorganic cyanide is suitably a water soluble cyanide, especially a cyanide salt such as an alkali metal or alkaline earth metal cyanide. Potassium and sodium cyanides are favoured.

The liquid medium is preferably aqueous and especially a two-phase system consisting of an aqueous phase containing the inorganic cyanide and an organic phase comprising a water-immiscible solvent, such as chloroform, in which the compound of formula (II) is, at least, partially soluble. When a two-phase system is used, it is desirable to have present a phase transfer catalyst.

By the term "phase transfer catalyst" is meant a substance which, being at least partly present in or wetted by a first (usually organic) phase promotes reaction between a reactant in the first phase with another reactant which it transfers from a second (usually aqueous) phase to the first phase. After reaction the phase transfer catalyst is released for transferring further reactant. Phase transfer catalysts are reviewed by E. V. Dehmlow in Angewante Chemie (International Edition) Vol. 13, No. 3, 1974, page 170. Other reviews are by Jozef Dockx in Synthesis 1973 at pages 441–456 and by C. M. Starks in the Journal of the American Chemical Society (93) 1, Jan. 13, 1971, pages 195–199.

Suitably the phase transfer catalyst is a quaternary ammonium salt preferably containing at least one long chain N-alkyl group. An example is cetrimide (hexadecyltrimethylammonium bromide).

It may be possible to use a one-phase liquid medium provided the medium is capable of dissolving significant amounts of both reactants. A liquid medium comprising water and a water-miscible solvent, such as acetone, may be suitable.

The temperature of reaction will depend on the particular reactants involved and nature of the liquid medium used but will generally be in the range of from 20° C. to 100° C., preferably 40° to 80° and especially 50° to 70° C. at atmospheric pressure. In an aqueous chloroform medium, the reaction is conveniently carried out under reflux at about 60° C.

The compounds of formula (II) which will normally be used in the invention are 1,2,4,5-tetrachloro-3,6-dinitrobenzene, 1,2,3,4-tetrachloro-5,6-dinitrobenzene and 1,2,3,5-tetrachloro-4,6-dinitrobenzene. These may be obtained by the di-nitration of the appropriate tetrachlorobenzene, as described, for example, in Recueil des Travaux Chimique des Pays Bas 44 (1925), 851 and 857, or, in the case of the first mentioned compound, by the nitration of the commercially available product Tecnazene (1,2,4,5-tetrachloro-3-nitrobenzene). Also included in the compounds of formula (II) are 1,2,4,5-tetrachloro-3-cyano-6-nitrobenzene, 1,2,3,4-tetrachloro-5-cyano-6-nitrobenzene and 1,2,3,5-tetrachloro-4-cyano-6-nitrobenzene which are intermediate products of the process of the invention when starting from the corresponding di-nitro compounds.

It would appear that the ortho and para nitrocyanotetrachlorobenzenes react with $CN^-$ significantly faster than do the ortho and para dinitrotetrachlorobenzenes so that the intermediate nitrocyanotetrachlorobenzenes are not readily isolated. In contrast, the meta nitro-cyanotetrachlorobenzene can be isolated and further reaction to the meta dicyanotetrachlorobenzene requires more severe process conditions, e.g. higher temperatures and longer reaction times.

When using a two-phase liquid medium, the process of the invention is conveniently carried out by stirring together and heating under reflux a mixture of the compound of formula (II), a water-soluble cyanide, a phase transfer catalyst, water and a water-immiscible solvent. The progress of reaction can be followed by analysing periodically samples of the organic phase. When no further reaction takes place the organic layer is separated, washed with water and the solvent removed by evaporation to leave the compound of formula (I).

The amount of inorganic cyanide used need be only that required by the stoichiometry of the reaction, or a small excess (e.g. 5% mol excess). Larger excesses might be expected to increase the rate of reaction without harming the reaction products.

The proportion of water to solvent is thought not to be critical. It seems necessary only that there should be sufficient of each to dissolve significant amounts of both reactants. At higher concentrations, increased reaction rates might be expected. Typically, equal volumes are used.

The compounds of formula (I) find use in, for example, the synthesis of certain compounds having pesticidal activity. In this regard the preferred compounds may be used to prepare intermediate compounds of the formula (III):

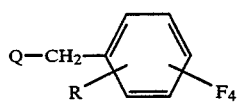

in which Q is hydroxy, halo, preferably bromo or chloro, or a quaternary ammonium group, and R, which is attached to the benzene ring in a position ortho or para to the methylene group, is alkyl or alkenyl.

The present invention is of particular value in preparing from the commercially available 1,2,4,5-tetrachlorobenzene, compounds of formula (IV)

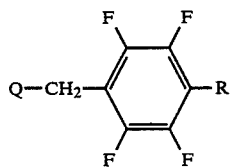

in which Q and R have the meanings defined hereinabove.

Thus 2,3,5,6-tetrachloroterephthalodinitrile, prepared from 1,2,4,5-tetrachloro-3,6-dinitrobenzene according to the process of the present invention, may be fluorinated with potassium fluoride in a polar aprotic solvent to form the corresponding tetrafluoroterephthalodinitrile. The dinitrile may be converted to the corresponding benzene dicarboxylic acid by acid hydrolysis and the acid decarboxylated by heating in a polar aprotic solvent to provide 1,2,4,5-tetrafluorobenzene.

A compound of formula (V)

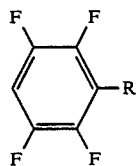

may be prepared by reacting the 1,2,4,5-tetrafluorobenzene with an organometallic reagent such as alkyl lithium, and decomposing the reaction product with an appropriate alkyl or alkenyl halide. The compound of formula (V) may then be carboxylated (for example by the use of an organometallic reagent such as alkyl lithium followed by decomposition of the reaction product with carbon dioxide) and subsequently reduced to the compound of formula (IV), in which Q is hydroxy, using an appropriate reducing reagent, for example, lithium aluminium hydroxide. Further reaction with a source of positive halogen such as an N-chloro- or N-bromoimide, for example N-chlorosuccinimide and N-bromosuccinimide, provides the compound (IV) in which Q is halo, and, if desired, a quaternary ammonium salt can be formed by treatment with a tertiary amine, for example, a trialkylamine such as triethylamine.

The invention is illustrated by the following Examples 1 to 3 in which percentages are by weight.

EXAMPLE 1

1,2,4,5-Tetrachloro-3,6-dinitrobenzene (1.53 g, 0.005 mol), potassium cyanide (0.65 g, 0.01 mol), cetrimide (0.05 g), water (5 ml) and chloroform (5 ml) were stirred and heated under reflux (60° C.). Samples of the organic phase were removed at intervals and examined by glc analysis (5 ft column, 5% OV 225). After 2 hours, there was estimated to be present in the chloroform a ca.90% yield of tetrachloroterephthalodinitrile.

Glc peak area ratios were

| Structure | Ratio |
|---|---|
| CN/Cl/Cl/Cl/Cl/CN | 88.1% |
| NO₂/Cl/Cl/Cl/Cl/NO₂ | 6.7% |
| NO₂/Cl/Cl/Cl/Cl/CN | suspected 5.2% |

The mixture was cooled to ambient temperature and chloroform (50 ml) added. The organic layer was separated and washed with water (50 ml). Solvent was removed at the pump, from the organic layer, to leave a brown solid. The IR spectrum of this solid showed C=N at 2240 cm$^{-1}$ and some residual NO$_2$ at 1550 to 1560 cm$^{-1}$. The overall IR spectrum was very similar to that of authentic tetrachloroterephthalodinitrile. Glc-mass spectrometry confirmed that the major component was $C_6Cl_4(CN)_2$: m/e 264 (4Cl$^{35}$). The suspected intermediate $NO_2C_6Cl_4CN$ was confirmed: m/e 284 (4Cl$^{35}$).

EXAMPLES 2 AND 3

Using a procedure similar to that described in Example 1 the following Examples were carried out.

| Example | Starting Material | Process time | Product | Yield (%) |
|---|---|---|---|---|
| 2 | 1,2,3,4-tetrachloro-5,6-dinitrobenzene | 24 hours | 1,2,3,4-tetrachloro-5,6-dicyanobenzene* | 53 |
| 3 | 1,2,3,5-tetrachloro-4,6-dinitrobenzene | 3 days | 1,2,3,5-tetrachloro-4-cyano-6-nitrobenzene | 30 |

*Very little 1,2,3,4-tetrachloro-5-cyano-6-nitrobenzene was identified.

I claim:

1. A process for the preparation of a compound of formula (I):

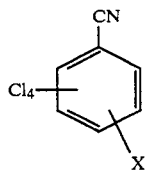

(I)

in which X is CN or, when X is in a position *meta* to the CN group in formula (I), CN or NO₂, which process comprises reacting in a liquid medium a compound of formula (II):

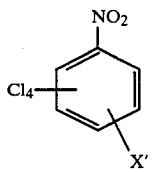

(II)

in which X', which is in a corresponding position to X, is CN or NO₂ with, in solution, an inorganic cyanide, whereby at least one NO₂ group is replaced by a cyano group.

2. A process according to claim 1 in which X and X' are in positions ortho or para to the CN group of formula (I) and NO₂ group of formula (II), respectively.

3. A process according to claim 2 in which X is CN and X' is NO₂.

4. A process according to claim 1 in which the inorganic cyanide is an alkali metal or alkaline earth metal cyanide.

5. A process according to claim 1 in which the liquid medium is a two-phase liquid system consisting of an aqueous phase containing the inorganic cyanide and an organic phase comprising a water-immiscible solvent in which the compound of formula (II) is, at least, partially soluble.

6. A process according to claim 5 in which a phase transfer catalyst is present.

7. A process according to claim 1 in which the reaction is carried out at a temperature of from 20° to 100° C.

* * * * *